United States Patent
Pope et al.

(10) Patent No.: US 6,200,308 B1
(45) Date of Patent: Mar. 13, 2001

(54) DYNAMIC COOLING OF TISSUE FOR RADIATION TREATMENT

(75) Inventors: Karl Pope, Belmont; Anthony J. Durkin, Watertown; James C. Hsia, Weston, all of MA (US)

(73) Assignee: Candela Corporation, Wayland, MA (US)

( * ) Notice: Subject to any disclaimer, the term of this patent is extended or adjusted under 35 U.S.C. 154(b) by 0 days.

(21) Appl. No.: 09/240,464

(22) Filed: Jan. 29, 1999

(51) Int. Cl.⁷ .................................................. A61B 18/18
(52) U.S. Cl. ...................... 606/9; 606/2; 606/11; 606/20; 606/23
(58) Field of Search .................. 606/2, 3, 9, 10, 606/11, 13–17, 20–26; 607/88, 89, 91–93

(56) References Cited

U.S. PATENT DOCUMENTS

| | | |
|---|---|---|
| 5,342,352 * | 8/1994 | Franken et al. .......................... 606/9 |
| 5,630,811 | 5/1997 | Miller . |
| 5,814,040 * | 9/1998 | Nelson et al. . |
| 5,817,089 | 10/1998 | Tankovich et al. . |
| 5,820,626 * | 10/1998 | Baumgardner . |
| 5,979,454 * | 11/1999 | Anvari et al. . |
| 5,997,530 * | 12/1999 | Nelson et al. . |

FOREIGN PATENT DOCUMENTS

WO 97/37723   10/1997   (WO) .
WO 99/27863 *  6/1999   (WO) .

* cited by examiner

Primary Examiner—Linda C. M. Dvorak
Assistant Examiner—Bryan K. Yarnell
(74) Attorney, Agent, or Firm—Testa, Hurwitz & Thibeault, LLP

(57) ABSTRACT

A method for performing radiation treatment of skin in connection with dynamic cooling of tissue, while minimizing or preventing occurrence of light flash during the treatment.

27 Claims, 7 Drawing Sheets

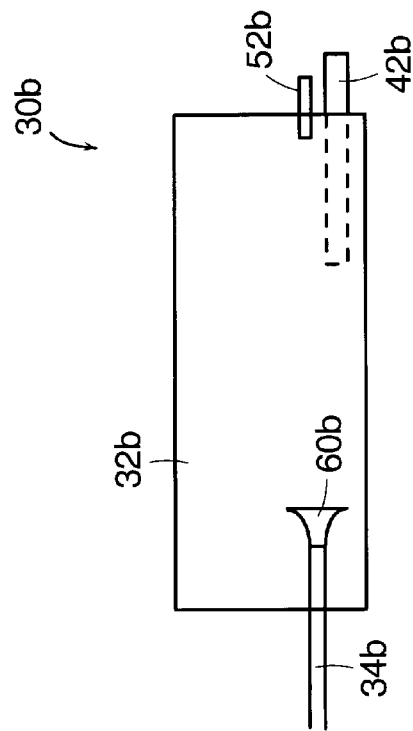
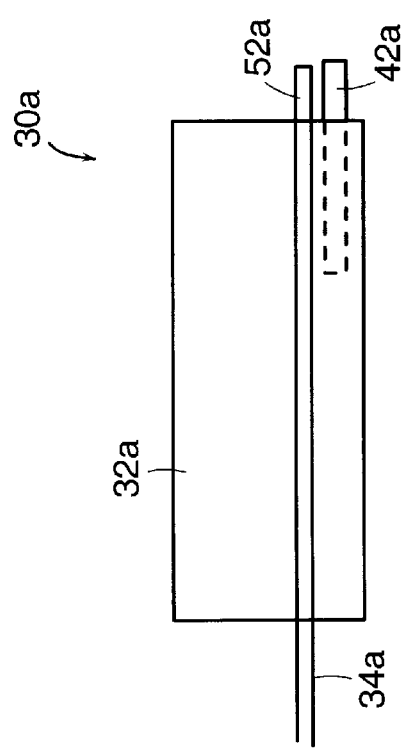

DYNAMIC COOLING OF TISSUE FOR RADIATION TREATMENT

FIELD OF THE INVENTION

This invention relates to radiation treatment of tissue. More specifically, this invention relates to an improved dynamic cooling device and method in connection with radiation treatment of tissue.

BACKGROUND

Radiation surgery has been successfully employed to treat tissue. Radiation surgery involves the application of radiation to tissue to remove or alter the condition of the tissue. Radiation can be generated in the form of light from a laser or a lamp such as a flash lamp, or heat from an RF source. Alternatively, radiation can be generated in the form of microwaves or ultrasound.

Laser surgery has been successfully employed to remove hair and to treat skin abnormalities such as vascular lesions. For example, in performing a laser surgery, a beam of laser light having a selected wavelength is applied to a targeted region of the skin to selectively destroy the cutaneous blood vessels or melanin depending on the application. When removing unwanted hair, a beam of laser light is applied to the targeted skin. The light penetrates deep into the dermal tissue region, where the light is absorbed by peri-follicular melanin, reaching the follicle, bulb, bulge, and vascular supply to eliminate unwanted hair and impede its growth. In treating vascular lesions such as a port wine stain, laser light is preferentially absorbed by the hemoglobin which is the major chromophore in the blood in the ectatic capillaries in the upper dermis. The light energy is converted to heat, causing thermal damage and thrombosis in the targeted vessels.

Laser treatments, however, can be painful to a patient. To reduce pain, the cooling of tissue has been employed during laser treatment. U.S. Pat. No. 5,814,040, incorporated herein by reference, describes cooling an epidermal tissue region while performing selective photothermolysis of selected buried chromospheres in biological tissues using a laser. This cooling procedure is known as dynamic cooling. In this procedure, an epidermal tissue region is cooled by spraying with a cryogen to establish a predetermined dynamic temperature profile. The epidermal and underlying dermal tissue regions are subsequently irradiated to thermally treat the dermal tissue region while leaving the epidermal tissue region substantially undamaged. Cooling the epidermal tissue region reduces pain suffered by the patient during the procedure, and permits application of higher dosage radiation.

The GentleLase™ laser treatment system for hair removal and treatment of vascular lesions manufactured by Candela Corporation (Wayland, Mass.) employs dynamic cooling technology. The GentleLase™ laser treatment system includes a control unit and a handpiece. The control unit includes a flashlamp excited long-pulse alexandrite laser, a source of HFC 134a liquid cryogen, and electronics for controlling the system. The handpiece receives the laser light and the cryogen from the control unit through a cable which includes an optical fiber, wires, a delivery tube and an electronically controlled valve. The handpiece delivers the cryogen and the laser to tissue being treated. In the procedure, a highly focused spray of HFC 134a cryogen is applied on the patient's skin for 20–100 milliseconds, and after waiting 0–3 milliseconds, the laser pulse is applied to the patient's skin.

Clinical tests have shown that in order to achieve a desirable low temperature profile (e.g. −30° C. to 25° C.) in the epidermal tissue region, a waiting period after applying the cryogen of up to about 250 milliseconds is needed before applying the laser pulses. The desirable low temperature profile can vary depending on the skin tone of the patient and the objective in cooling. Only a few degrees below normal skin temperature may be sufficient when treating a patient having a light skin tone. On the other hand, when treating a patient having a dark skin tone, cooling to −30° C. may be desired. One problem encountered during dynamic cooling of an epidermal tissue region with a waiting period of up to about 250 milliseconds is that a bright light flash not associated with normal laser treatment has been observed during the procedure. The bright light flash resembles a flame, and tends to frighten the patients and interfere with light transmission. Therefore, a shorter waiting period of about 3 milliseconds which may be insufficient to obtain an optimal low temperature profile, is presently used to suppress the abnormal light flash. It is expected that similar flashing problems can occur during radiation treatment using other radiation sources.

SUMMARY OF THE INVENTION

The present invention provides methods and systems for performing radiation treatment of skin, while dynamic cooling the epidermal tissue region and minimizing or preventing light flashes from occurring. The radiation treatment can include removal of hair or treatment of pigmentation abnormalities (e.g. vascular lesions, tattoos, etc.).

In one aspect, the invention features a method for performing radiation treatment of skin having an epidermal tissue region and a dermal tissue region. In one embodiment, the epidermal tissue region is cooled by applying a cryogenic fluid to the epidermal tissue region. A gas flow is directed in the general direction of the epidermal tissue region to remove at least a portion of the cryogenic fluid applied to the epidermal tissue region. The skin is irradiated with a radiation source to treat the dermal tissue region subsequent to removing at least a portion of the cryogenic fluid. This method has been found to minimize or prevent an abnormal light flash from occurring during the laser treatment.

In one detailed embodiment, a non-reactive gas flow is directed in the general direction of the epidermal tissue region. The non-reactive gas flow can comprise air, nitrogen, or $CO_2$. In another embodiment, a gas flow is directed in the general direction of the epidermal tissue region prior to and during application of the cryogenic fluid. In another detailed embodiment, skin is irradiated between 5 and 500 milliseconds, and more preferably between 50 and 200 milliseconds after applying the cryogenic fluid to the epidermal tissue region. In another detailed embodiment, a cryogenic liquid is applied to the epidermal tissue region and a cryogenic vapor formed, through the evaporation of the cryogenic liquid, is removed. In yet another detailed embodiment, the cryogenic fluid comprises a fluorocarbon compound having a ratio of fluorine to fluorine and hydrogen which is greater than about 0.75. The fluorocarbon compound is selected from a group consisting of: tetrafluoromethane; hexafluoroethane; octafluoropropane; chlorotrifluromethane; chloropentafluoroethane; dichlorodifluoromethane; 1,2-dichlorotetrafluoroethane; 1,1,1,2,3,3,3,-heptafluoropropane; pentafluoroethane; 2-chloro-1,1,1,2-tetrafluoroethane; trifluoromethane; 1,1,1,2,3,3-hexafluoropropane; and 2,2-dichloro-1,1,1-trifluoroethane.

In another embodiment, the method of performing radiation treatment of skin comprises the following steps. A first pulse of cryogenic fluid is applied to an epidermal tissue region for a first time period. After waiting a delay period of a predetermined time interval, a second pulse of cryogenic liquid is applied to the epidermal tissue region for a second time period. The delay period is sufficient to allow the first pulse of cryogenic fluid to cool the epidermal tissue region to reach a desired temperature profile. The skin is irradiated to treat an underlying dermal tissue region either during or immediately after application of the second pulse of cryogenic liquid, thereby minimizing or preventing an abnormal light flash from occurring during treatment.

In one detailed embodiment, a first pulse of cryogenic liquid is sprayed to the epidermal tissue region for a time period in the range from 10 milliseconds to 150 milliseconds, and a second pulse of cryogenic liquid is sprayed to the epidermal tissue region for a time period in the range from about 5 milliseconds to about 20 milliseconds after waiting a delay period in the range from about 10 milliseconds to about 500 milliseconds. In another detailed embodiment, the skin is irradiated within 5 milliseconds of applying the second pulse of cryogenic liquid. In still another detailed embodiment, the skin is irradiated within 3 milliseconds of applying the second pulse of cryogenic liquid.

In another aspect, the invention features an apparatus having a radiation source for performing a radiation treatment of skin having an epidermal tissue region adjacent a dermal tissue region. The apparatus includes a first fluid delivery device for delivering a cryogen to the epidermal tissue region, a device for delivering radiation to the skin to treat the dermal tissue region, and a second fluid delivery device for delivering a gas flow in the general direction of the epidermal tissue region to inhibit the chemical reaction leading to the bright light flash. The device for delivering radiation can be an optical device for delivering light.

In one embodiment, the second fluid delivery device surrounds the optical device. In another embodiment, the second fluid delivery device is substantially collinear with the first fluid delivery device. In another embodiment, the second fluid delivery device surrounds the first fluid delivery device. In another embodiment, the second fluid delivery device comprises a plurality of passageways substantially surrounding the optical device. In still another embodiment, the apparatus further includes a body, and the second fluid delivery device comprises an inlet for introducing the gas to the body and an outlet for removing the gas from the body. The gas entering the body through the inlet circulates within the body.

In another aspect, the invention features a handpiece attachable to a laser for performing laser treatment of skin. The handpiece includes a body, an optical device disposed inside the body for delivering a light beam from the laser to the skin to treat a dermal tissue region, a valve disposed inside the body for delivering a cryogen to an epidermal tissue region above the dermal region, and a fluid delivery device disposed inside the body for delivering a gas flow in the general direction of the epidermal tissue region to remove at least a portion of the cryogen delivered to the epidermal tissue region.

In one embodiment, the fluid delivery device substantially surrounds the optical device. In another embodiment, the valve is coupled to a cryogen tube and the fluid delivery device is substantially parallel to the cryogen tube. In another embodiment, the fluid delivery device comprises a plurality of passageways substantially surrounding the optical device. In still another embodiment, the valve is coupled to a cryogen tube and the fluid delivery device substantially surrounds the cryogen tube. In still another embodiment, the fluid delivery device includes an inlet for introducing the gas to the body and an outlet for removing the gas from the body. The gas introduced to the body through the inlet circulates within the body.

BRIEF DESCRIPTION OF THE DRAWINGS

This invention is described with particularity in the appended claims. The above and further advantages of this invention may be better understood by referring to the following description taken in conjunction with the accompanying drawings.

FIGS. 3A–3B show cross-sectional views of other embodiments of a handpiece of the radiation treatment system of FIG. 1.

DETAILED DESCRIPTION OF THE INVENTION

Figure 1:
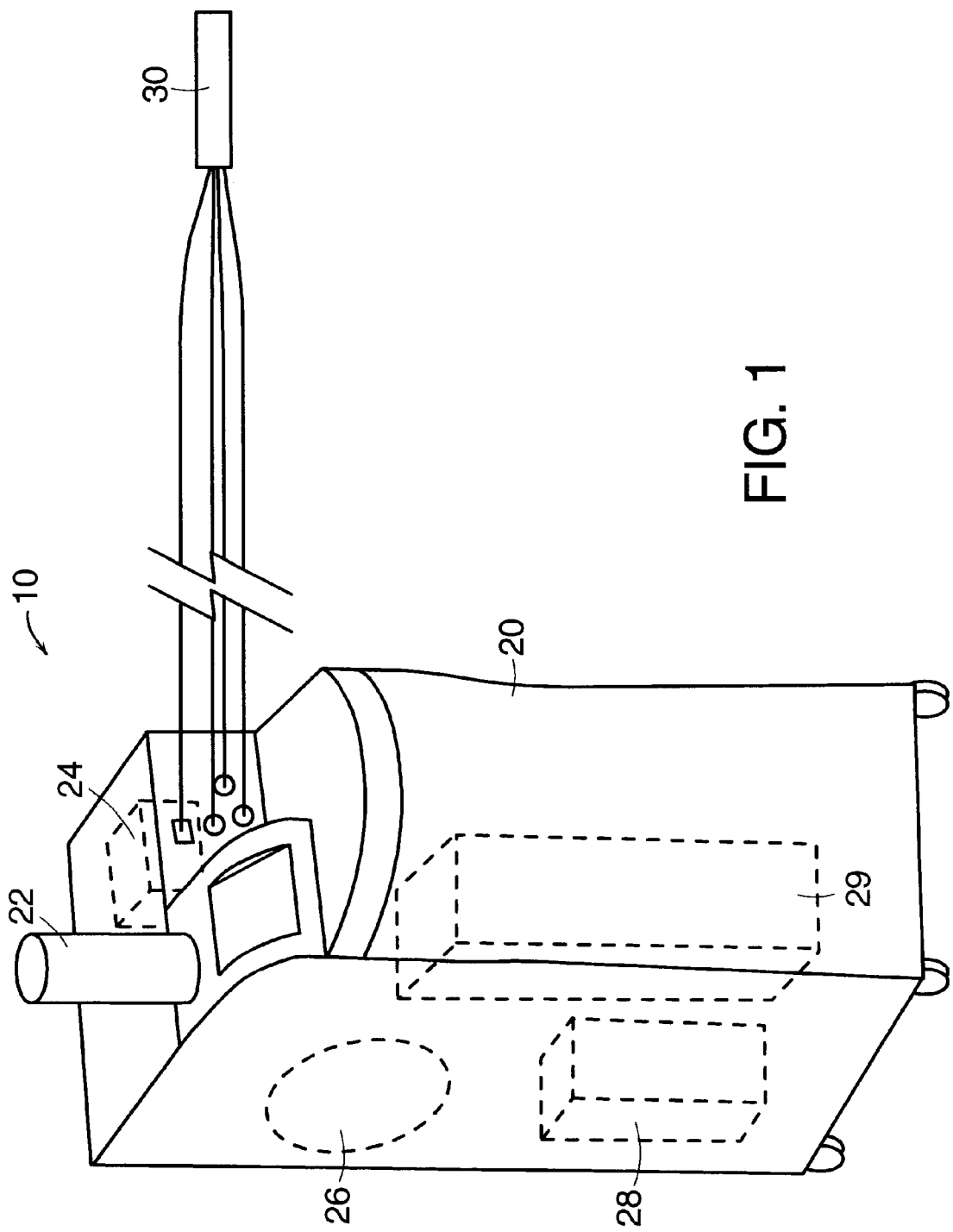
FIG. 1 shows a schematic diagram of an embodiment of a radiation system which provides dynamic cooling.

Referring to FIG. 1, a laser system 10 includes a control unit 20, and a handpiece 30. The control unit 20 includes a source of cryogen 22, a laser source 24, a source of gas 26, a power source 28 and electronics 29. The cryogen 22 is typically stored under pressure as a liquid. The radiation source 24 can be a laser source. In other embodiments, other light sources such as a flashlamp can be used to generate light. Alternatively, the sources which generate heat, microwave or ultrasound waves may be used. The source of gas 26 can be a non-reactive gas such as air or nitrogen. The power source 28 supplies power to initiate and run the system 10, and the electronics 29 control the application of the cryogen, the radiation, and the gas to a patient. The position of each component of the control unit 20 shown in FIG. 1 is exemplary only, and the components of the control unit 20 and handpiece 30 may be arranged according to other configurations.

Figure 2:
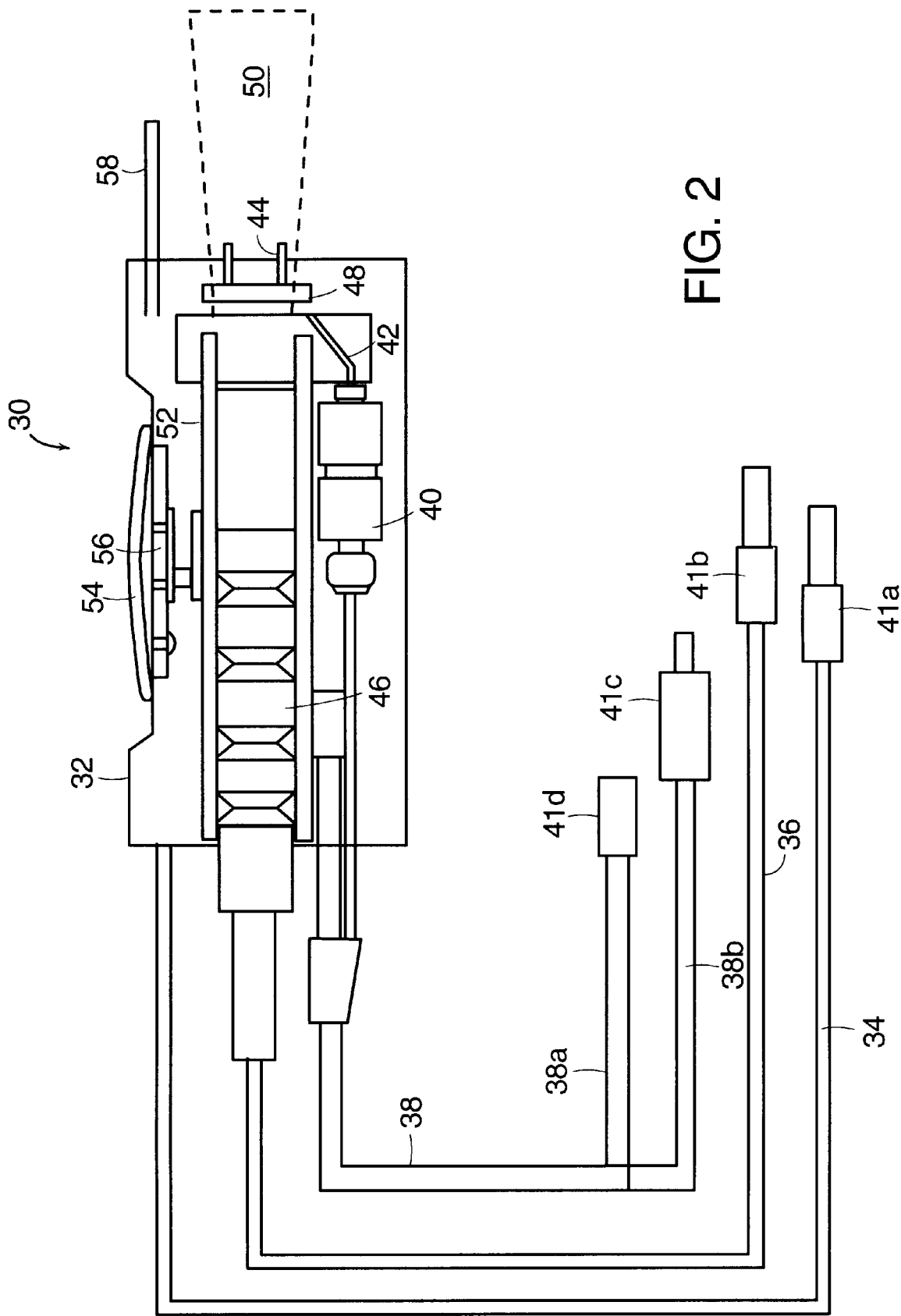
FIG. 2 shows a cross-sectional view of an embodiment of a handpiece of the radiation treatment system of FIG. 1.

Referring to FIG. 2, the handpiece 30 includes a handpiece body 32. A gas line 34 delivers gas from the gas source to the handpiece 30. In this embodiment, a fiber optic cable 36 delivers light from the source 24 to the handpiece 30. A cable 38 delivers cryogen from the cryogen source 22 to the handpiece 30. The cable 38 includes an electrical wire 38a which control opening and closing of a valve 40 located inside the handpiece body 32, and the cryogen delivery tube 38b. When the valve 40 is open, pulses of cryogen are released through the narrow metal cryogen tube 42. The cryogen tube 42 is angled to direct the cryogen pulses in the general direction of where a laser beam interacts with the skin. Laser light travels through the fiber optic cable to a fiber assembly 46 located inside the handpiece body 32. The fiber assembly 46 includes optics for focusing the laser light. The focused laser light passes through a glass window 48 and forms a beam path 50. The beam of laser light can be applied as pulses. Gas flows through the gas line 34 and a gas supply tube 52 located inside the handpiece body 42. In the embodiment of FIG. 2, the gas supply tube 52 surrounds the fiber assembly 46.

Figure 3D:
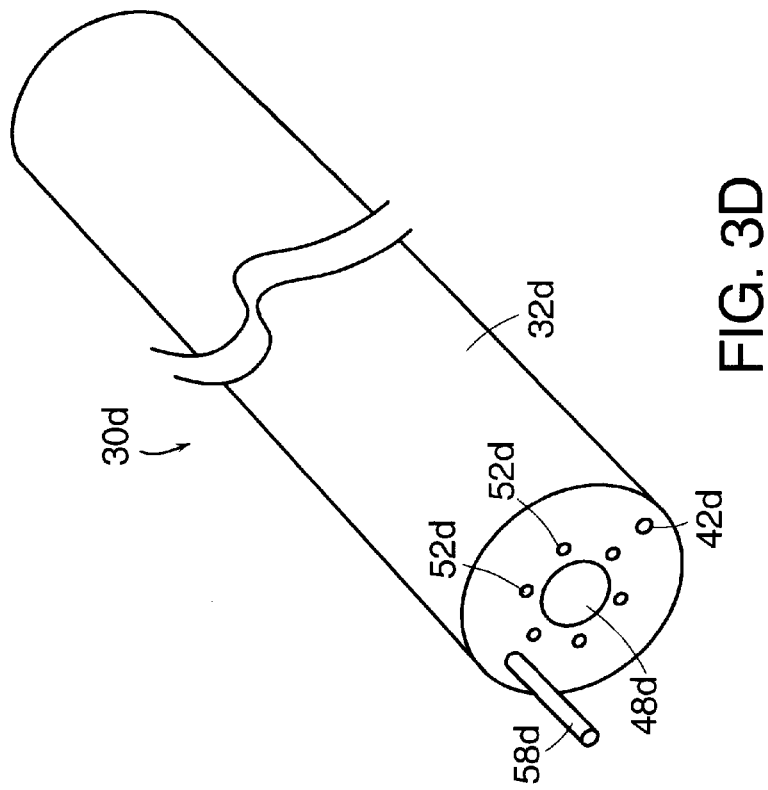
FIGS. 3C–3D show perspective views of other embodiments of a handpiece of the radiation treatment system of FIG. 1.
Figure 3C:
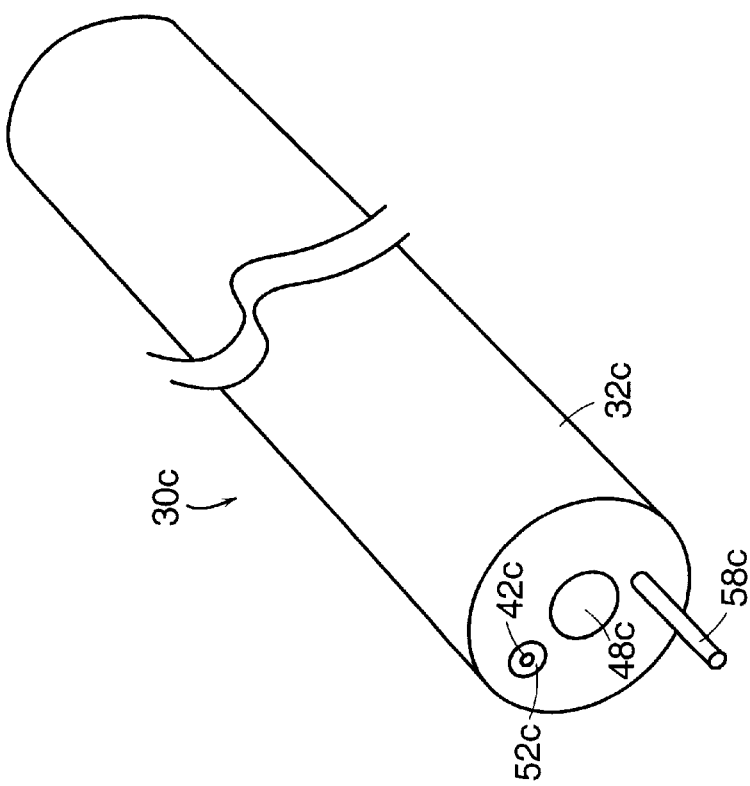

Referring to FIGS. 3A–3D, gas can be applied using other hardware configuration. In the embodiment of FIG. 3A, the gas supply line 34a continues through the handpiece body 32a, and gas is released through the gas dispenser 52a which is substantially parallel with the cryogen tube 42a. In this embodiment, gas and cryogen are released substantially co-linearly. In the embodiment of FIG. 3B, gas flows through the gas supply line 34b and a gas inlet 60b and floods into the handpiece body 32b. The gas flooded into the handpiece body 32b circulates within the handpiece body 32b and cools the body 32b, which may have been heated from the fiber assembly and light reflected from the skin. The gas is released through the gas outlet or the gas dispenser 52b. In the embodiment of FIG. 3C, a gas supply tube 52c surrounds the cryogen tube 42c, such that gas surrounds the cryogen when they are simultaneously released from the handpiece 32c. In the embodiment of FIG. 3D, the handpiece 32d includes multiple gas outlets 52d surrounding the fiber assembly (not shown). When the gas and the laser beam are simultaneously applied, the gas substantially surrounds the laser beam.

Referring to FIG. 2, the handpiece 30 further includes a button 54 which controls a switch 56. The switch 56 activates delivery of the laser, the cryogen and the gas. The handpiece 30 further includes a distance gauge 58. The distance gauge 58 comes in contact with the patient's tissue during laser treatment. The distance gauge 58 provides a predetermined desired distance between the handpiece 30 and the tissue of the patient. This predetermined distance controls the diameter of the laser beam 50. Each of the gas line 34, the optical cable 36, the electrical wire 38a, and the cryogen delivery tube 38b includes a connector 41a–41d respectively, for connecting to the control unit 20 shown in FIG. 1.

In one detailed embodiment, the laser source comprises a flashlamp excited long-pulse alexandrite laser. The laser pulses can have a repetition rate of one hertz (Hz) and a duration of 3 milliseconds (msec). The spot sizes can vary depending on the application. In one example, the spot sizes varies from 8 millimeters (mm) to 15 millimeters (mm). For an 8 mm spot size, the fluence can range from 20–100 $J/cm^2$. For a 10 mm spot size, the fluence can range from 20–60 $J/cm^2$. For a 12 mm spot size, the fluence can range from 6–40 $J/cm^2$. For a 15 mm spot size, the fluence can range from 6–30 $J/cm^2$.

Figure 4B:
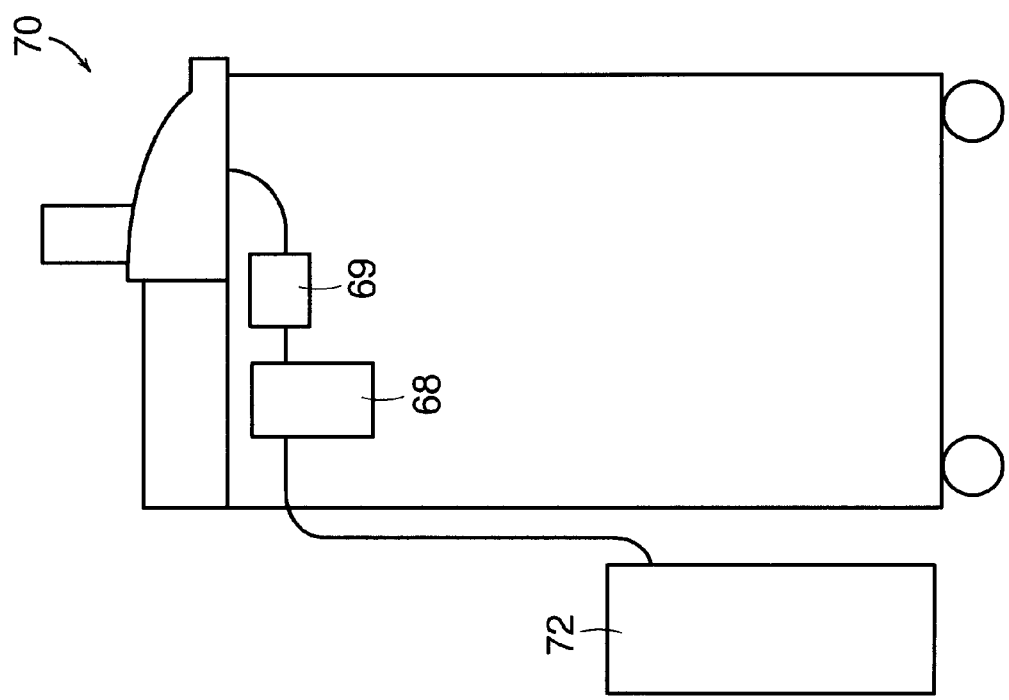
FIG. 4B shows a cross-sectional view of another embodiment of a control unit of the radiation treatment system of FIG. 1.
Figure 4A:
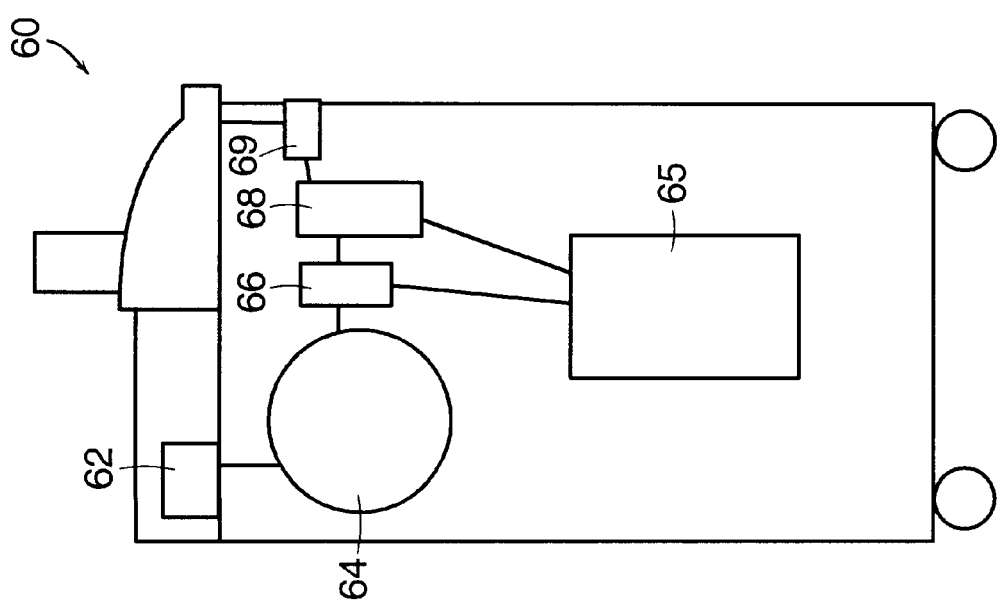
FIG. 4A shows a cross-sectional view of an embodiment of a control unit of the radiation treatment system of FIG. 1.

In one detailed embodiment, the controller 60 includes an air compressor 62, and an air reservoir 64 as shown in FIG. 4A. In this embodiment, air from the reservoir 64 passes through an air filter and water trap 66, a flowmeter and actuator 68, and an on/off valve 69. Air passing through the filter and water trap 66, and the flowmeter and actuator 68 is chilled with an air chiller 65. The actuator 68 and the on/off valve 69 control application of air. The valve 69 provides intermittent air flow. Alternatively a reservoir 72 external to the controller 70 can be used to store air as shown in FIG. 4B. In this embodiment, the compressor may not be needed. In another detailed embodiment, a continuous air flow may be applied. In this embodiment, application of air is controlled by an actuator 68 without the valve 69.

As described previously, an abnormal light flash has been observed when an epidermal tissue region is cooled with a cryogen prior to application of laser pulses. The light flash is more prominent as the time delay between the application of the cryogen and the laser pulses increases.

Although the exact nature of what causes light flashing is not known, a light flash has been observed where a combination of an initiator, laser pulse, and a cryogenic vapor exists. An initiator is a dark object, such as hair. It is believed that flashing may be caused by heating the initiator with the laser, which releases energy that is subsequently absorbed by cryogenic vapor molecules, causing the molecules to chemically react. Chemical reaction of cryogenic vapor molecules creates Carbon soot as a by product. Since Carbon soot is dark in color, it further functions as an initiator propagating additional light flashes. Flashing has been observed when R134a (tetrafluroethane) has been used as a cryogen.

Figure 5:
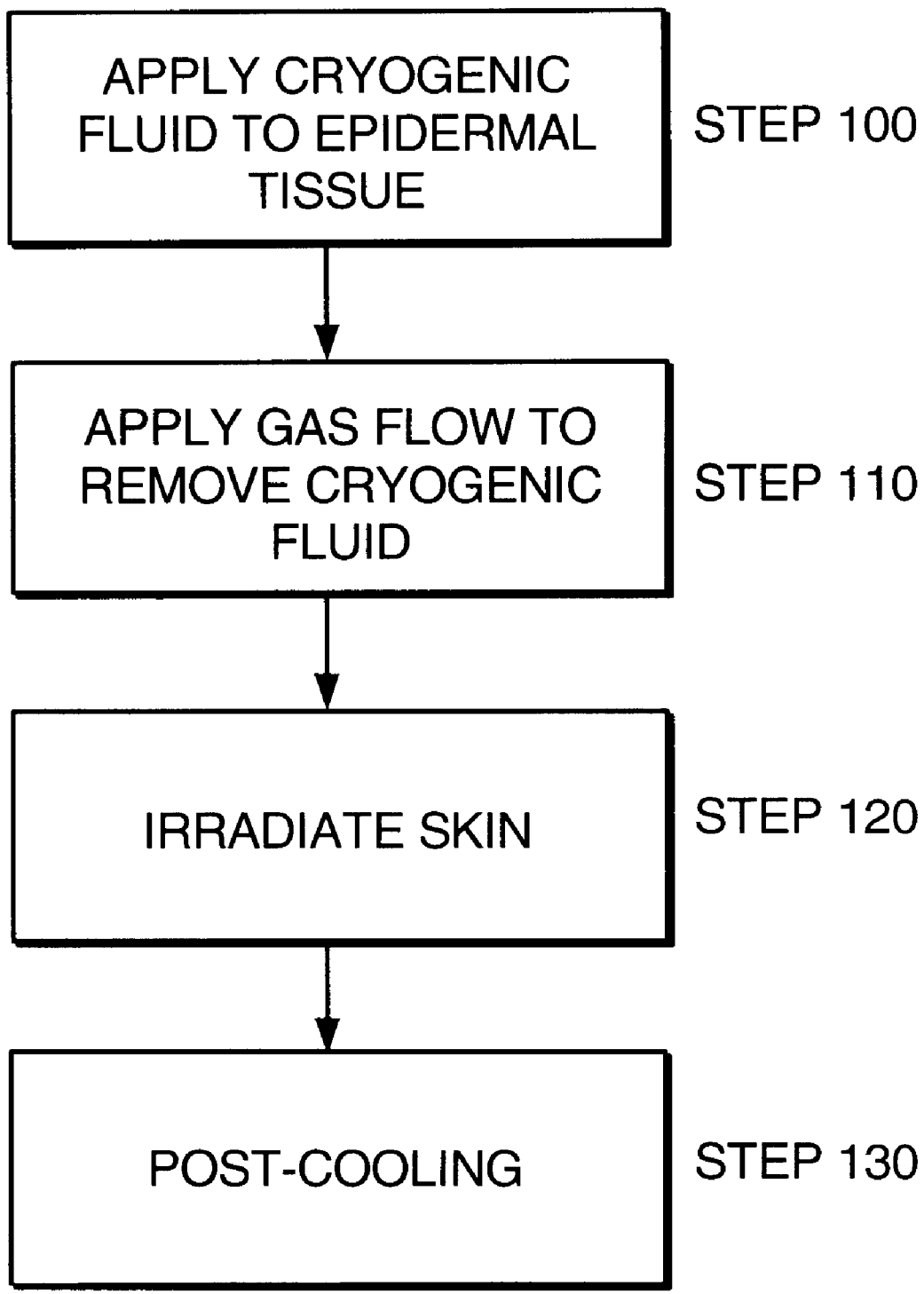
FIG. 5 shows a flow chart illustrating one embodiment of a method of performing radiation treatment of skin.

The present invention features several methods of performing laser treatment of skin, while minimizing or preventing occurrences of light flash. In one embodiment, the method includes the steps shown in FIG. 5, which uses the system described in FIGS. 1 through 4B. According to this method, an epidermal tissue region is cooled by applying a cryogenic fluid to the epidermal tissue region (step 100). A gas flow is applied in the general direction of the epidermal tissue region to remove at least a portion of the cryogenic fluid applied to the epidermal tissue region (step 120). The gas flow rate is greater than about 10 liters/minute. The skin is irradiated with a laser beam, to treat the underlying dermal tissue region (step 120).

In this embodiment, removing at least a portion of the cryogenic fluid prior to irradiating the dermal tissue region prevents light flash from taking place (step 120). The cryogenic fluid can be removed by applying or blowing a non-reactive gas to the epidermal tissue region. An example of an appropriate non-reactive gas, includes but is not limited to air and nitrogen. The application of the gas flow can begin prior to, during, or subsequent to the cooling step. In one embodiment, step 100 comprises spraying a cryogenic liquid to the epidermal tissue region and step 120 comprises removing cryogenic vapor formed through expansion of the cryogenic liquid. In this embodiment, application of the gas flow prevents flashing by removing both vapor molecules which chemically react, reaction products which sustain further reaction, and contaminants on the surface of the epidermal tissue which can participate as initiators.

Application of the gas flow can also beneficially contribute to cooling of the epidermal tissue region. In particular, application of the gas flow is believed to increase the speed at which the cryogenic liquid evaporates, and therefore increases the speed at which the epidermal tissue region is cooled. In another embodiment, the temperature of the gas flow is intentionally lowered to further reduce the temperature of the epidermal tissue region. The gas may be pre-cooled to below about 20° C. The method of FIG. 5 can further include the step of post-cooling the epidermal tissue region by applying a cryogenic fluid to the epidermal tissue region after the irradiation step (step 130). The post-cooling step can minimize damage to normal tissue caused by irradiation and accelerate healing of the treated tissue.

In one detailed embodiment, the irradiation step (step 120) takes place between 5 and 500 milliseconds after applying the cryogen to the epidermal tissue region. This delay period is sufficient to achieve the desired low temperature profile in the epidermal tissue region. This delay period, however, does not cause a light flash due to the removal step (step 110). Without the removal step, this delay period is likely to be sufficient for some cryogenic liquids such as R134a to vaporize and react, thereby causing a light flash. However, with the removal step, light flash is inhibited. In a preferred embodiment, the irradiation step takes place about 50 to 200 milliseconds after applying the cryogen to the epidermal tissue region.

Figure 6:
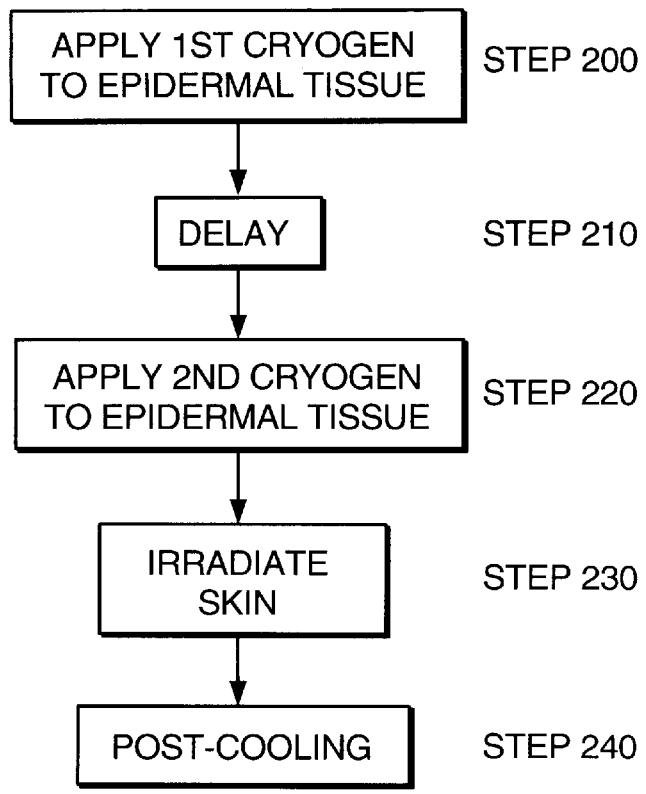
FIG. 6 shows a flow chart illustrating another embodiment of a method of performing radiation treatment of skin.

In another embodiment, the method for performing a laser treatment of skin, while preventing a light flash, comprises the steps shown in FIG. 6. A first pulse of cryogenic fluid is applied to the epidermal tissue region for a first time period (step 200). After waiting a delay period of a predetermined time interval (step 210), a second pulse of cryogenic fluid is applied to the epidermal tissue region (step 220). In this embodiment, the term "first pulse" refers to a first group of pulses, which may be one or more pulses. Likewise, the term "second pulse" refers to a second group of pulses, which may be one or more pulses. The skin is irradiated to treat the dermal tissue region after the application of the second pulse of cryogenic (step 230). In one detailed embodiment, the second pulse of cryogenic fluid comprises a cryogenic liquid and the irradiation step takes place either during or immediately after the application of the second pulse of cryogenic fluid. The second pulse of cryogen inhibits the first pulse of cryogen from reacting and creating a light flash. In addition, the application of the second pulse assists with cooling of the epidermal tissue region, and allows the first pulse of cryogenic fluid to be applied for a shorter time period in order to achieve a desired low temperature profile for the epidermal tissue region.

In one detailed embodiment, the first pulse of cryogenic liquid is sprayed to the epidermal tissue region for a time period ranging from 10 to 150 milliseconds. The waiting period ranges from about 10 to about 500 milliseconds. The second pulse of cryogenic liquid is sprayed to the epidermal tissue region for a time period ranging from 5 to 20 milliseconds. The skin is irradiated within 5 milliseconds after applying the second pulse of liquid cryogen. In one example, a first pulse of cryogenic liquid is applied for about 20 to 100 milliseconds, and after waiting 100 to 200 milliseconds, the second pulse of cryogenic liquid is applied for 5 to 20 milliseconds. In this example, skin is irradiated within 3 milliseconds of applying the second pulse of cryogenic liquid.

Figure 7:
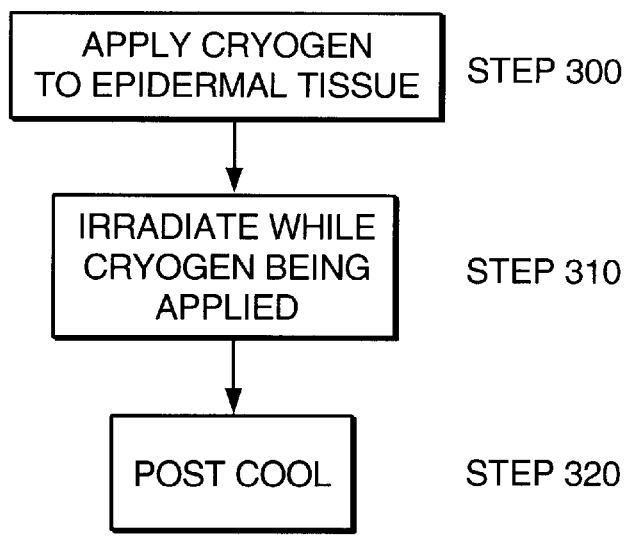
FIG. 7 shows a flow chart illustrating another embodiment of a method of performing radiation treatment of skin.

In another embodiment, the method of performing laser treatment comprises the steps shown in FIG. 7. In this embodiment, the cryogenic fluid is first sprayed to the epidermal tissue region (step 300), and the skin is irradiated to treat the dermal tissue region while the cryogen is still being sprayed to the epidermal tissue region (step 310). In one detailed embodiment, the irradiation step begins before the liquid cryogen spray terminates. The method can further include the step of post cooling the treated skin (step 320).

The present invention further contemplates the use of cryogen sources which are less likely to cause a light flash. A conventional cryogen sources such as R134a (tetrafluroethane) tends to dissociate quickly and cause a light flash. In one embodiment, a cryogen source comprises a fluorocarbon compound where the ratio of fluorine to fluorine and hydrogen is equal to or greater than about 0.75. In another embodiment, a cryogen source comprises a fluorocarbon compound where the ratio of chlorine and fluorine to chlorine, fluorine and hydrogen is equal to or greater than about 0.75. In addition, the fluorocarbon compound has a boiling point of less than about 35° C. Examples of such compounds are provided in the following table:

| Name | C | H | Cl | F | BP (° C.) | Enthalpy of vaporization BTU/L; kJ/mol | Ratio of F/(F + H) | Ratio of (Cl + F)/(Cl + F + H) |
|---|---|---|---|---|---|---|---|---|
| Tetrafluoromethane | 1 | 0 | 0 | 4 | −128 |  | 1 | 1 |
| Hexafluoroethane | 2 | 0 | 0 | 6 | −78 | 50; 16 | 1 | 1 |
| Octafluoropropane | 3 | 0 | 0 | 8 | −38 | 45.28; 19 | 1 | 1 |
| Chlorotrifuoromethane (R13) | 1 | 0 | 0 | 3 | −81 | 63; 15 | 1 | 1 |
| Chloropentafluoroethane | 2 | 0 | 1 | 5 | −39 |  | 1 | 1 |
| Dichlorodifluoromethane (R12) | 1 | 0 | 2 | 2 | −30 | 68; 19 | 1 | 1 |
| 1,2-Dichlorotetrafluoroethane (R114) | 2 | 0 | 2 | 4 | 4 | 61.1; 24 | 1 | 1 |
| 1,1,1,2,3,3,3-Heptafluoropropane (R227ea) | 3 | 1 | 0 | 7 | 20 | 57; 22 | 0.88 | 0.88 |
| pentafluoroethane (R125) | 2 | 1 | 0 | 5 | −49 | 61.5; 17 | 0.83 | 0.83 |
| 2-chloro-1,1,1,2,-tetrafluoroethane (R124) | 2 | 1 | 1 | 4 | −12 | 71.3; 23 | 0.80 | 0.83 |
| Trifluoromethane (R23) | 1 | 1 | 0 | 3 | −82 | 100; 16 | 0.75 | 0.75 |
| 1,1,1,2,3,3,-Hexafluoropropane (R236ea) | 3 | 2 | 0 | 6 | 7 |  | 0.75 | 0.75 |
| 2,2,-dichloro-1,1,1,-trifluoroethane (R123) | 2 | 1 | 2 | 3 | 28 | 79.1; 28 | 0.75 | 0.83 |

Equivalents

While the invention has been particularly shown and described with reference to specific preferred embodiments, it should be understood by those skilled in the art that various changes in form and detail may be made therein without departing from the spirit and scope of the invention as defined by the appended claims.

What is claimed is:

1. A method for performing radiation treatment of skin having an epidermal tissue region adjacent a dermal tissue region, the method comprising:
    a) cooling the epidermal tissue region by applying a cryogenic fluid to the epidermal tissue region;
    b) directing a gas flow in general direction of the epidermal tissue region subsequent to step a) to remove at least a portion of the cryogenic fluid applied to the epidermal tissue region; and
    c) irradiating the skin with a radiation beam to treat the dermal tissue region subsequent to removing at least a portion of the cryogenic fluid to prevent a light flash during the irradiation step.

2. The method of claim 1 wherein step b) comprises directing a non-reactive gas flow in the general direction of the epidermal tissue region.

3. The method of claim 2 wherein step b) comprises blowing air in the general direction of the epidermal tissue region.

4. The method of claim 2 wherein the non-reactive gas comprises nitrogen.

5. The method of claim 1 wherein step b) comprises directing a gas flow in the general direction of the epidermal tissue region prior to and during application of the cryogenic fluid.

6. The method of claim 1 wherein step c) comprises irradiating the skin for between about 5 milliseconds and 500 milliseconds after applying the cryogenic fluid to the epidermal tissue region.

7. The method of claim 1 wherein step a) comprises applying a first pulse of cryogenic fluid to the epidermal tissue region for a first time period and waiting a delay period of a predetermined time interval before applying a second pulse of cryogenic fluid to the epidermal tissue region for a second time period.

8. The method of claim 7 wherein the delay period is in a range from about 10 milliseconds to about 500 milliseconds.

9. The method of claim 7 wherein the first time period comprises from about 20 milliseconds to 100 milliseconds and the second time period comprises from about 5 milliseconds to 20 milliseconds.

10. The method of claim 1 wherein step a) comprises applying a cryogenic liquid and step b) comprises removing a cryogenic vapor formed through evaporation of the cryogenic liquid.

11. The method of claim 1 wherein step b) comprises removing a plurality of contaminants over an outer surface of the epidermal tissue region.

12. The method of claim 1 wherein step b) comprises directing a gas flow at a rate of greater than about 10 liters per minute.

13. The method of claim 1 further comprising pre-cooling the gas flow to a temperature below about 20° C.

14. The method of claim 1 wherein step a) comprises applying of cryogen comprising a fluorocarbon compound wherein a ratio of fluorine to fluorine and hydrogen is equal to or greater than about 0.75.

15. The method of claim 14 wherein the fluorocarbon compound is selected from a group consisting of: tetrafluromethane; hexafluoroethane; octafluoropropane; chlorotrifluromethane; chloropentafluoroethane; dichlorodifluoromethane; 1,2-dichlorotetrafluoroethane; 1,1,1,2,3,3,3,-heptafluoropropane; pentafluoroethane; 2-chloro- 1,1,1,2-tetrafluoroethane; trifluoromethane; 1,1,1,2,3,3-hexafluoropropane; and 2,2-dichloro- 1,1,1-trifluoroethane.

16. The method of claim 1 wherein step c) comprises irradiating the dermal tissue region to remove a hair.

17. The method of claim 1 wherein step c) comprises irradiating with a laser light.

18. The method of claim 1 further comprising d) post-cooling the epidermal tissue region by applying a cryogenic fluid to the epidermal tissue region after the irradiation step.

19. A method of performing radiation treatment of skin having an epidermal tissue region adjacent a dermal tissue region, the method comprising:
    a) applying a first pulse of cryogenic fluid to the epidermal tissue region for a first time period;
    b) waiting a delay period of a predetermined time interval before applying a second pulse of cryogenic liquid to the epidermal tissue region for a second time period, the delay period being sufficient to allow the first pulse of cryogenic fluid to cool the epidermal tissue region to reach a desired temperature; and
    c) irradiating the skin to treat the dermal tissue region during or immediately after application of the second pulse of cryogenic liquid, thereby preventing a light flash during the irradiation step.

20. The method of claim 19 wherein step a) comprises spraying a cryogenic liquid to the epidermal tissue region for a time period in a range from about 10 milliseconds to 150 milliseconds.

21. The method of claim 19 wherein step b) comprises spraying a cryogenic liquid to the epidermal tissue region for a time period in a range from about 5 milliseconds to about 20 milliseconds.

22. The method of claim 19 wherein the delay period is in a range from about 10 milliseconds to about 500 milliseconds.

23. The method of claim 19 wherein step c) comprising irradiating the skin within 5 milliseconds of applying the second pulse of cryogenic liquid.

24. The method of claim 19 wherein step a) comprises applying a first pulse of cryogenic liquid comprising a fluorocarbon compound wherein a ratio of fluorine to fluorine and hydrogen is equal to or greater than about 0.75; and step b) comprises applying a second pulse of cryogenic liquid comprising the fluorocarbon compound.

25. The method of claim 24 wherein the fluorocarbon compound comprises a compound selected from a group consisting of tetrafluoromethane; hexafluoroethane; octafluoropropane; chlorotrifluromethane; chloropentafluoroethane; dichlorodifluoromethane; 1,2-dichlorotetrafluoroethane; 1,1,1,2,3,3,3,-heptafluoropropane; pentafluoroethane; 2-chloro-1,1,1,2-tetrafluoroethane; trifluoromethane; 1,1,1,2,3,3-hexafluoropropane; and 2,2-dichloro-1,1,1-trifluoroethane.

26. The method of claim 19 wherein step c) comprises irradiating the dermal tissue to remove hair.

27. The method of claim 19 wherein step c) comprises irradiating with a laser light.

* * * * *